United States Patent [19]
Roitman

[11] Patent Number: 5,569,209
[45] Date of Patent: Oct. 29, 1996

[54] NEEDLELESS TRANSFER SYSTEM

[75] Inventor: Alan L. Roitman, Woodbury, N.Y.

[73] Assignee: Jemm Tran-Safe Systems, Inc., Woodbury, N.Y.

[21] Appl. No.: 361,128

[22] Filed: Dec. 21, 1994

[51] Int. Cl.⁶ ................................................ A61M 5/00
[52] U.S. Cl. ........................ 604/190; 604/68; 604/905; 604/406; 604/256; 251/149.4
[58] Field of Search .................. 251/149.4, 149.9; 137/549, 550; 604/283, 68, 82, 83, 85–91, 245, 403, 905, 405, 406, 414, 190, 181, 187, 246, 247, 256

[56] References Cited

U.S. PATENT DOCUMENTS

| | | | |
|---|---|---|---|
| 2,913,995 | 11/1959 | Brenner | 137/549 |
| 3,920,002 | 11/1975 | Dye et al. | 251/149.4 |
| 4,328,948 | 5/1982 | Pearl, II | 251/149.4 |
| 5,211,638 | 5/1993 | Dudar et al. | 604/283 |
| 5,376,073 | 12/1994 | Graves et al. | 604/283 |
| 5,464,399 | 11/1995 | Boettger | 604/283 |

*Primary Examiner*—Corrine M. McDermott
*Assistant Examiner*—Ronald K. Stright, Jr.
*Attorney, Agent, or Firm*—Allen R. Morganstern, Esq.

[57] ABSTRACT

This invention relates to a new and improved design associated with the fabrication and construction of a needleless transfer system wherein through the use of a unique valve mechanism there is avoided the necessity to utilize a needle in conjunction with a syringe for purposes of transferring and/or injecting a liquid medium from one environment into another environment. By having the valve mechanism comprise a hollow enclosure which has contained therein a compressible structure which acts both as a filter and as a mechanism to allow for the selective flow of a liquid medium through the system in a singular direction, the capabilities of the needleless transfer system are achieved.

17 Claims, 3 Drawing Sheets

NEEDLELESS TRANSFER SYSTEM

BACKGROUND AND OBJECTS OF THE INVENTION

This invention relates to a new and improved design associated with the fabrication and construction of a needleless transfer system. In accordance with the invention, through the unique design of the valve mechanism used in accordance with the invention, there is achieved a needleless transfer system wherein one is able to transmit in one direction a liquid medium without the necessity of utilizing a needle, as is the common practice to date.

With the growing concerns of transmitting, either through inadvertence, accident, or otherwise, a deadly or highly contagious disease, be it AIDS, or otherwise, there has developed a growing need within the medical and health care professions of developing a means by which the use of needles in combination with a syringe is diminished, as related to the many tasks associated with the treatment of a patient. As is and as has been the common practice in the medical community to date, a syringe with a needle attached thereto has been utilized to remove from storage containers various medicines, solutions, and/or the like. By pushing the needle portion thereof through the element sealing the container (be it a cork-like substance or otherwise) and then drawing out into the interior of said syringe the various medicines, solutions, and/or the like, and then upon withdrawing the needle attached to said syringe from said container said needle attached to said syringe is then inserted into either another container, tubing system, and/or the like, there occurs a series of tasks that expose a health care participant to accidental injury from the needle. Inherent in said process is the risk of having the needle puncture the skin of the party carrying out said process and the risk of contaminating said party with a deadly or highly debilitating disease and/or foreign substance not intended for introduction into the body of the health care participant.

It is in keeping with this invention to achieve the ability to transmit medicines, solutions, and the like, from one environment to another without the necessity of utilizing a needle attached to a syringe so as to achieve same and thereby eliminate the concerns of accidental contamination of an individual.

Although it is known in the prior art that such risks exist in the utilization of a needle in combination with a syringe to achieve the administering of medicines, solutions, and the like, none of the prior art structures address themselves to the specific embodiment and the advantages and expediencies of the present invention.

With regard to said prior art which addresses itself to the above concerns, it should be noted that the following patents evidence awareness of the problem seeking to be overcome as well as relate to certain structures that seek to accomplish same, however, said prior art neither anticipates nor otherwise teaches the present invention. More particularly, the prior art referred to above is as follows: U.S. Pat. No. 4,128,098, entitled "Valved Spike Transfer Device", issued to Bloom et al. on Dec. 5, 1978; U.S. Pat. No. 4,354,492, entitled "Medical Administration Set With Backflow Check Valve", issued to McPhee on Oct. 19, 1982; U.S. Pat. No. 4,759,756, entitled "Reconstitution Device", issued to Forman et al. on July 26, 1988; U.S. Pat. No. 4,936,841, entitled "Fluid Container", issued to Aoki et al. on Jun. 26, 1990; U.S. Pat. No. 4,950,254, entitled "Valve Means for Enteral Therapy Administration Set", issued to Anderson et al. on Aug. 21, 1990; U.S. Pat. No. 5,125,415, entitled "Syringe Tip Cap with Self-Sealing Filter", issued to Bell on Jun. 30, 1992; U.S. Pat. No. 5,036,992, entitled "Medicine Vial Cap for Needleless Syringe", issued to Mouchawar et al. on Aug. 6, 1991; U.S. Pat. No. 3,831,629, entitled "Check Valve", issued to Mackal et al. on Aug. 27, 1974; U.S. Pat. No. 4,181,233, entitled "One-Way Valve Stopper", issued to Gouveia on Jan. 1, 1980; U.S. Pat. No. 3,904,059, entitled "Sterile Closure for Solution Bottles", issued to Bellamy, Jr. et al. on Sep. 9, 1975; and U.S. Pat. No. 5,202,093, entitled "Sealing Cap with a One Way Valve Having Semi-Cylindrical Valve Closure Springs", issued to Cloyd on Apr. 13, 1993.

In keeping with the invention, it is a specific object thereof to create a new and improved needleless transfer system that is simple in construction and whose use is facilitated by its design.

It is another object of the present invention to create a new and improved needleless transfer system wherein there is overcome the need and/or necessity to utilize a needle in conjunction with a syringe to withdraw, transmit, and/or administer medicines, solutions, and/or the like, in conjunction with the care and/or treatment of a patient.

It is another object of the present invention to provide a new and improved needleless transfer system wherein there is additionally provided within the needleless transfer system a means to filter any medium passing therethrough.

It is another object of the present invention to provide a new and improved needleless transfer system wherein multiple needleless transfer systems can be utilized in conjunction with the treatment of a single individual so as to allow for the combining of medicines, solutions, and/or the like, within the same environment of treatment.

It is another object of the present invention to provide a new and improved needleless transfer system wherein the flow of a medium therethrough can be selectively determined.

It is another object of the present invention to provide a new and improved needleless transfer system wherein the utilization of the needleless transfer system will not contaminate the environment from which a medium is removed or into which a medium is injected.

It is another object of the system to provide a simplified means of transferring fluid media without tile need for multiple and/or complex systems and/or devices.

It is another object of the invention to provide a complete system in and of itself not requiring other independent devices and/or components which utilizes present day standards thereby negating the need for re-tooling and/or changing of standard devices in current use.

The objects and advantages of the invention are set forth in part herein and in part will be obvious herefrom, or may be learned by practice of the invention, the same being realized and attained by means of the instrumentalities and combinations pointed out in the appended claims.

The invention consists in the novel parts, constructions, arrangements, combinations and improvements herein shown and described.

DESCRIPTION OF PREFERRED EMBODIMENT

Figure 2:
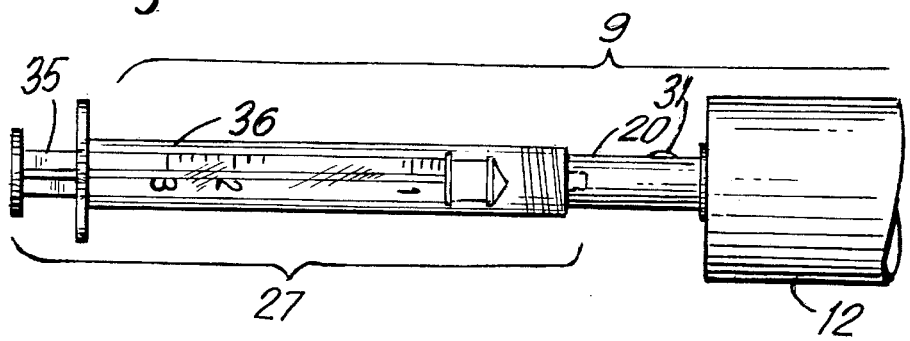
FIG. 2 is a partial front view of the needleless transfer system depicting the mechanical coupling in accordance with the invention of a syringe to one end of the valve mechanism depicted in FIG. 1.
Figure 3:
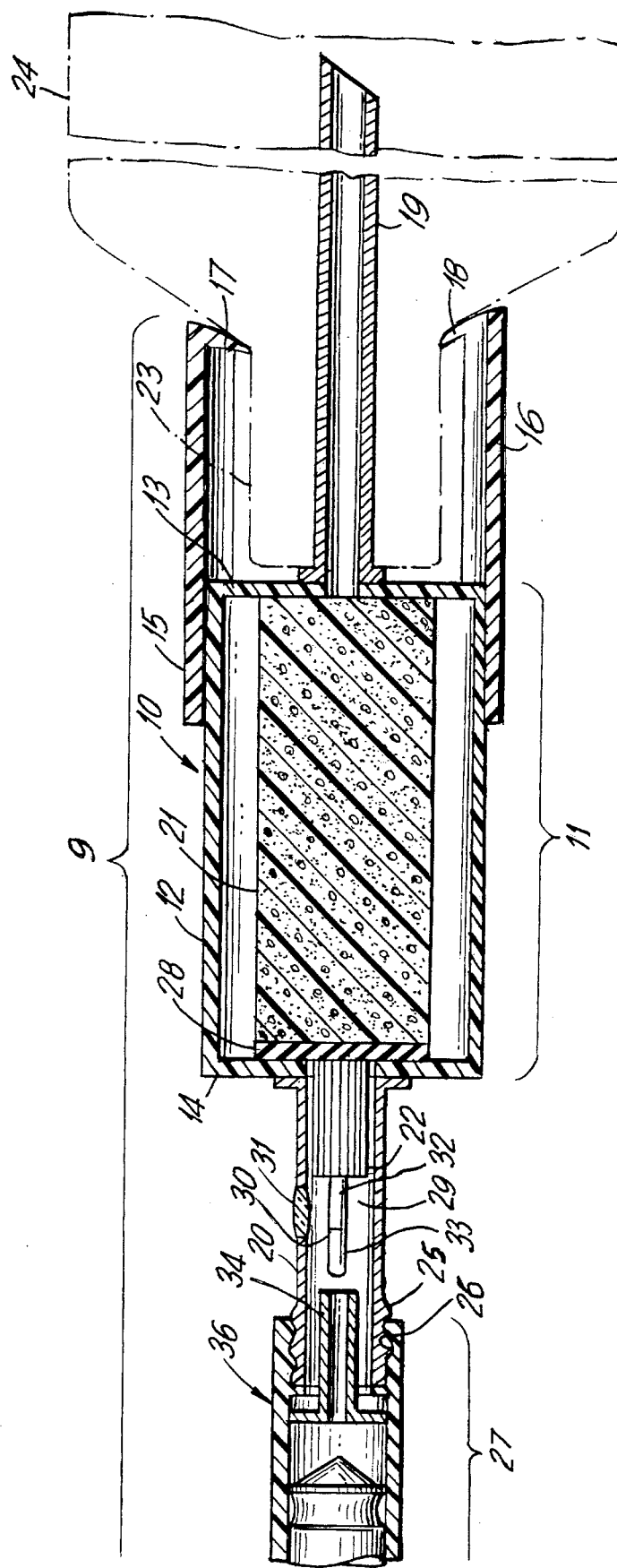
FIG. 3 is a partial cross-sectional view of the valve mechanism depicted in FIG. 1 taken along line 3—3 wherein the valve mechanism is in its closed position and is in mechanical interfit in accordance with the invention with a syringe shown in partial cross section as well as additionally depicting the valve mechanism coupled to the mouth of a container.

Reference is now herein made to FIG. 3 wherein there is illustrated a cross-sectional view of valve mechanism 10 constructed in accordance with the invention as utilized in needleless transfer system 9. As depicted in FIG. 2, needleless transfer system 9 comprises valve mechanism 10 in combination with syringe 27, syringe 27 being an item well known in the prior art.

Figure 1:
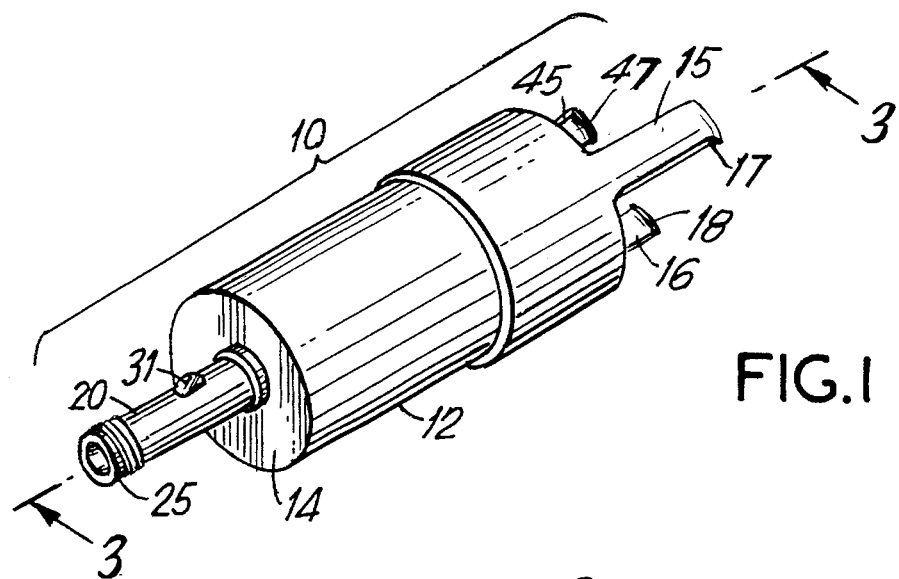
FIG. 1 is three-dimensional perspective view of the valve mechanism utilized in conjunction with the needleless transfer system.
Figure 4:
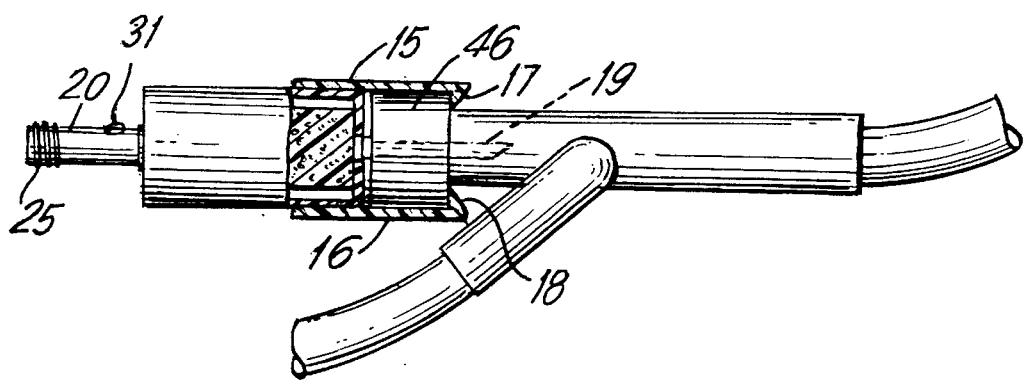
FIG. 4 is a partial cross-sectional view of the valve mechanism depicted in FIG. 1 in mechanical interfit with an intravenous line as applicable to its utilization during medical treatment.
Figure 5:
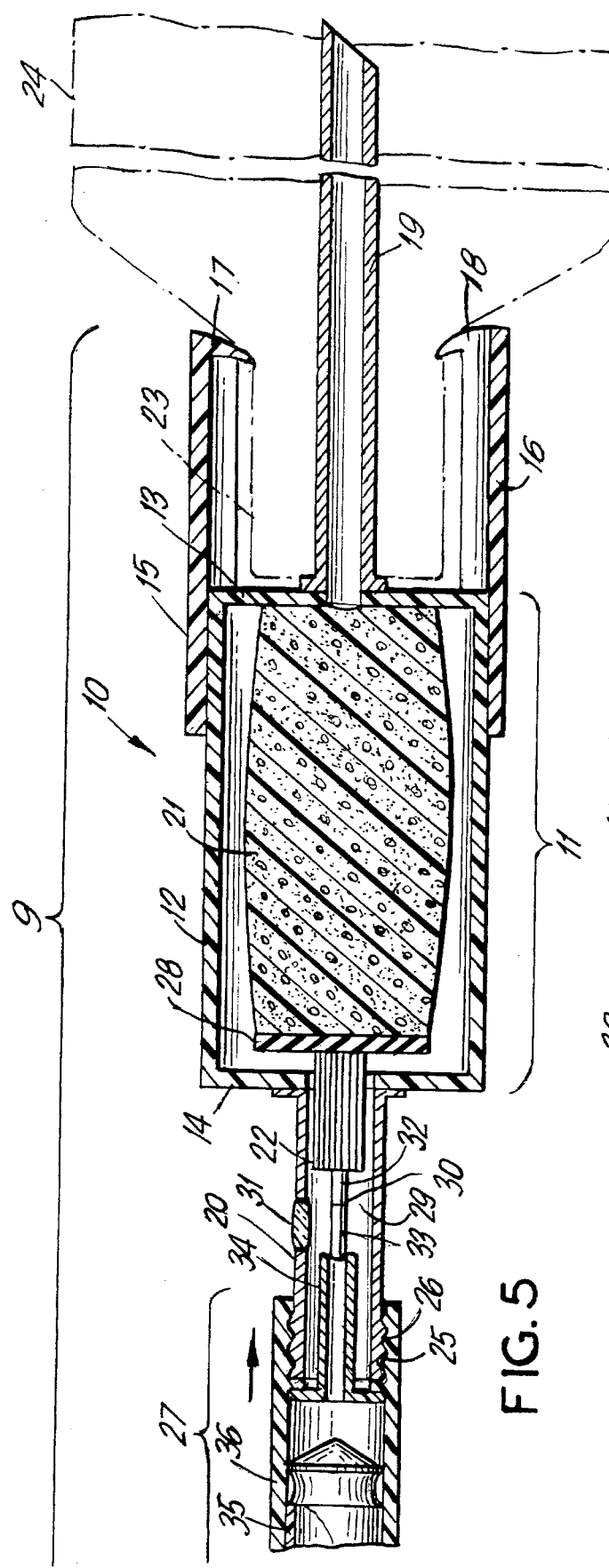
FIG. 5 is a partial cross-sectional view of the valve mechanism depicted in FIG. 3 in mechanical interfit with a syringe in accordance with the invention wherein the valve mechanism is in an open position.
Figure 6:
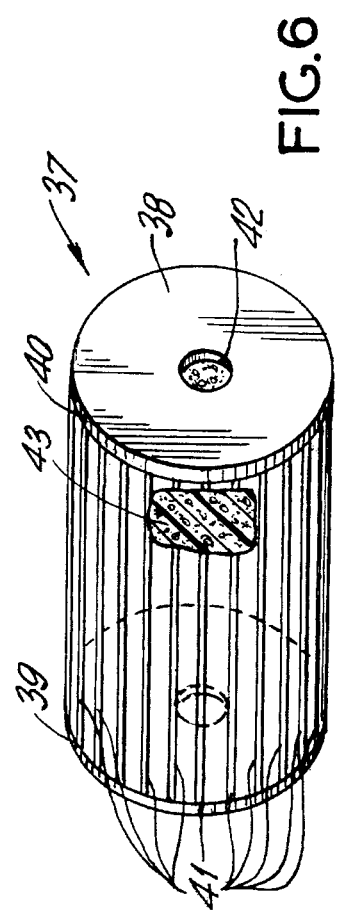
FIG. 6 is a three-dimensional perspective view evidencing an alterative embodiment to filter member 21 which is capable of being utilized in place of filter member 21 in the valve mechanism of the needleless transfer system depicted in FIGS. 3, 4 and 5.

As illustrated in FIG. 3, valve mechanism 10 comprises hollow enclosure 11 which defines a hollow cylindrical structure having a cylindrical wall 12 closed on both ends by circular wall member 13 and circular wall member 14 so as to define an airtight cylindrical cavity. Structurally affixed to the outer surface of cylindrical wall 12 is clamp member 15 and clamp member 16, clamp member 15 being formed so that the end thereof not affixed to cylindrical wall 12 is formed to define angular hook member 17. Similarly, clamp member 16 is formed so that the end thereof not affixed to cylindrical wall 12 is formed to define angular hook member 18. In conjunction with the above, it should be noted that as illustrated in FIG. 1, valve mechanism 10 has equally spaced about the circumference of cylindrical wall 12 three clamp members, namely clamp member 15, clamp member 16 and clamp member 45, all being identical in construction so as to allow for the structural affixing of valve mechanism 10 to either a container as illustrated in FIG. 3, FIG. 5 and FIG. 6 of the drawings or to allow for the structurally affixing of valve mechanism 10 to an intravenous port as illustrated in FIG. 4 of the drawings. Clamp member 15, clamp member 16 and clamp member 45, along with angular hook members 17, 18 and 47 respectively, are designed so as to effectuate a detachable mechanical grip of valve member 10 onto neck 23 of container 24 as illustrated in FIGS. 3 and 5 or to intravenous port member 46 of FIG. 4 so as to allow for said valve mechanism 10 to remain structurally affixed thereto once clamped thereon.

It should additionally be noted that it is within the scope of this invention that any means to achieve the selective mechanical affixing and removal of valve mechanism 10 to and/or from a container such as container 24, as illustrated in FIGS. 3 and 5 or intravenous port member 46 as illustrated in FIG. 4 is contemplated herein. More particularly, in accordance with the above, clamp members 15, 16 and 45 can be replaced by a screw-on-type or snap-on-type structure capable of being selectively attached to the neck of container 24 and/or intravenous port member 46, such structures being well known in the prior art.

As further illustrated in FIG. 3, there is protruding from circular wall member 13 at the center thereof and at right angles to circular wall member 13, hollow spike member 19, hollow spike member 19 forming an airtight seal with cylindrical wall member 13 and defining at its spiked end a structure that is capable upon the application of force parallel to the axis of hollow spike member 19 to penetrate through material that is utilized as a stopper and/or other sealant normally utilized to seal the neck of a container, intravenous port member of an intravenous system or the like. Protruding from cylindrical wall member 14 at the center thereof and at right angles to circular wall member 14 is hollow cylindrical neck member 20 which is structurally affixed at one of its ends in an airtight manner to circular wall member 14. The other end of hollow cylindrical neck member 20 defines an exterior threading 25 capable of mechanical interfit in an airtight fashion with interior threading 26 appearing on cylindrical shaft member 36 of syringe 27 such that upon the insertion of the tip member 34 of syringe 27 as illustrated in FIG. 3 into neck member 20, and upon the clockwise rotation of said syringe 27, there occurs a mechanical interfit between syringe 27 and neck member 20 that is air tight and leak proof due to the mechanical interfit of interior threading 26 of syringe 27 with the exterior threading 25 of neck member 20.

Contained within hollow enclosure 11 and positioned adjacent to cylindrical wall 12 is filter member 21 which defines a shape cylindrical in form and compatible with that of the interior cavity defined by the interior surfaces of cylindrical wall 12, circular wall member 13 and circular wall member 14. It should be noted that filter member 21 is of a structural composition such that it is capable of being compressed upon the application of a force along its axial length as well as to allow for the passage through its structure of a liquid medium while filtering same. Although this invention should not be considered limited to the following, it is envisioned that in the preferred embodiment hereof, filter member 21 can be constructed from any one of the following materials, to wit, nitrocellulose, cellulose acetate, nylon, polysulfane, or other suitable plastic material of a resilient nature that offers porosity for the purpose of allowing for the passage of a liquid medium therethrough.

In further keeping with the invention, and as depicted in FIG. 3, there is structurally affixed to filter member 21, washer member 28. In keeping with the invention, washer member 28 can be fabricated from any one of a number of compositions of material, the basic characteristics thereof being such that washer member 28 is capable of sealing off by way of an air tight and/or liquid tight seal the interior of hollow enclosure 11 from the passage of any liquid introduced into neck member 20. As long as filter member 21 is not compressed by mechanical pressure directed parallel to the axis of filter member 21 and against washer member 28 so as to cause washer member 28 to move away from cylindrical wall member 14, filter member 21 in its uncompressed state provides sufficient pressure against washer member 28 so as to force washer member 28 up against cylindrical wall member 14 so as to provide an air and/or liquid tight seal at that location.

Protruding from the surface of washer member 28 and structurally affixed thereto is shaft member 22. Shaft member 22 is cylindrical in shape and structurally affixed to washer member 28 at the center of washer member 28. Shaft member 22 protrudes into the cylindrical interior opening 29 of neck member 20. Structurally affixed to shaft member 22 and axily aligned with shaft member 22 is indicator shaft 30. Indicator shaft 30 is color coded so as to indicate through window element 31 formed within neck member 20 the positioning of shaft member 22. As indicated in FIG. 3, indicator shaft 30 has two separate and distinct colored portions, one colored portion thereof in accordance with the invention being indicated by a red colored surface 32 and the remaining portion of indicator shaft 30 having a green colored surface 33.

As indicated in FIG. 3, when washer member 28 is in its sealed position adjacent to circular wall member 14, no liquid is allowed to pass through valve mechanism 10 and red colored surface 32 of indicator shaft 30 is able to be observed through window element 31. Upon observing a red indication through window element 31, one is able to determine that valve mechanism 10 is in a closed and thus non-operative position. It should be noted that window element 31 can be fabricated from any one of a number of materials, be it glass, clear plastic, or the like, and is affixed in an air tight manner within the opening formed in neck member 20 designed to receive window element 31 such that there is provided a means readily available to determine when valve mechanism 10 is in an open position or a closed position. As illustrated in FIG. 3, valve mechanism 10 is in a closed position and is evidenced by the fact that red colored surface 32 of indicator shaft 30 is positioned directly under window element 31. Upon referring to FIG. 5, valve mechanism 10 is in an open position as evidenced by the fact that green colored surface 33 of indicator shaft 30 is positioned under window element 31.

As indicated in FIG. 5, upon the insertion of tip member 34 of syringe 27 into neck member 20, tip member 34 of said syringe comes into physical contact with indicator shaft 30. Upon the rotational threading of said syringe 27 in conjunction with neck member 20, tip member 34 of syringe 27 advances inward in axial alignment with shaft member 22. As indicated in FIG. 5, upon syringe 27 being mechanically coupled to neck member 20 by the rotational threading and mechanical intercoupling of interior threading 26 of syringe 27 with exterior threading 25 of neck member 20, syringe 27 becomes mechanically attached to valve mechanism 10 in accordance with the implementation of the needleless transfer system in an air tight/liquid tight coupling.

Upon the initial coupling of syringe 27 to neck member 20, tip member 34 is not initially in direct mechanical contact with indicator shaft 30 as depicted in FIG. 3. As depicted in FIG. 3, syringe 27 is in initial mechanical coupling with neck member 20 such that washer member 28 is mechanically positioned physically adjacent to circular wall member 13, thereby effectively closing off valve mechanism 10.

Upon the further rotational movement of syringe 27 so as to cause the further intercoupling of interior threading 26 with exterior threading 25, as depicted in FIG. 5, tip member 34 is caused to axially move towards washer member 28 so as to be mechanically forced up against indicator shaft 30. Upon the further rotation of syringe 27 as referred to above, there occurs the further axial movement of tip member 34 towards washer member 28 such that indicator shaft 30, shaft member 22 and washer member 28 are all forced to mechanically move such that washer member 28 is forced away from the interior surface of wall member 13 as indicated in FIG. 5. As a result, filter member 21 is compressed and thus valve mechanism 10 is in its open position so as to allow for the flow of a liquid, as illustrated in FIG. 5. As illustrated in FIG. 5, a liquid is able to flow either from syringe 27 through neck member 20, through hollow enclosure 11 via filter member 21 and through hollow spike member 19 into the interior of container 24, or in the alternative, a liquid can be withdrawn from the interior of container 24 by having said liquid flow through hollow spike member 19, through filer member 21, through hollow enclosure 11, through the hollow interior of neck member 20 and into the interior of syringe 27.

The direction of flow of a liquid in accordance with the above and as referred to with regard to FIG. 5, is determined by whether or not syringe 27, as illustrated in FIG. 2, either has its plunger 35 initially positioned inserted all the way within the shaft member 36 of syringe 27 such that upon the movement of plunger 35 in a direction so as to draw itself out from within shaft member 36 of syringe 27 a vacuum is created within syringe 27 so as to in effect suck out a liquid from container 24 as a result thereof, or in the alternative, upon having syringe 27 have its plunger 35 withdrawn from shaft member 36 of syringe 27 and there being contained within shaft member 36, a liquid, and upon then threading syringe 27 onto neck member 20, as indicated in FIG. 5, such that washer member 28 is forced into the open position of valve mechanism 10, there is then created the ability to inject from syringe 27 into container 24 a liquid in accordance with the invention, all of the above not requiring the utilization of a needle.

In keeping with the invention, it should also be noted that as illustrated in FIG. 4, valve mechanism 10 can be utilized in conjunction with an intravenous drip system, as therein illustrated. In utilizing valve mechanism 10 in conjunction with an intravenous drip system, clamp member 15, 16 and 45 snap onto the exterior of intravenous port member 46 as illustrated in FIG. 4 after hollow spike member 19 has been forced through intravenous port member 46.

Furthermore, it should also be noted that in keeping with the invention, filter member 21, as illustrated in FIGS. 3, 4 and 5 can be replaced with an alternate filter mechanism 37, as illustrated in FIG. 6.

More particularly, filter mechanism 37 comprises a hollow cylindrical wall member 40 having circular end member 38 and circular end member 39 as therein depicted, wall member 40 of filter mechanism 37 having formed therein and running from said circular end members 38 and 39 a series of slits 41 such that upon the compression of filter mechanism 37 by causing circular end member 39 to move towards circular end member 38, the slit openings 41 formed through wall member 40 of filter member 37 part and otherwise open up wider than is the case in filter mechanism 37's uncompressed state so as to allow for the free flow of liquid from either the interior of filter mechanism 37 to the exterior thereof or vice versa all in keeping with the invention.

In further keeping with the invention, filter mechanism 37, in accordance with the alternative embodiment thereof, as hereinabove set forth, is of such a design and construction so as to be readily substituted for filter member 21. In accordance therewith, filter mechanism 37, upon its utilization in valve mechanism 10, as would be evident upon viewing of FIG. 5, has hollow spike member 19 structurally affixed to circular end member 38 at opening 42 while circular end member 39 of filter mechanism 37 is structurally affixed to washer member 28.

For all practical purposes, filter mechanism 37 is designed so as to provide an alternative embodiment to filter member 21 of valve mechanism 10 as depicted in FIGS. 3, 4 and 5 wherein filter mechanism 37 is basically substituted for filter member 21. It should further be noted that contained within the interior of filtering mechanism 37 as depicted in FIG. 6 is a compression of filtering material 43 capable of removing impurities from a liquid in a similar fashion to that which is accomplished by filter member 21 as depicted in FIGS. 3, 4 and 5. As herein preferably embodied, filtering material 43 can be any one of the following compositions of material, to wit, nitrocellulose, glass paper or any material currently used in filtration of liquids to the specified porous requirements needed for the particular use.

It will be understood that the foregoing general description and the following detailed description as well are exemplary and explanatory of the invention, but are not restrictive thereof.

The accompanying drawings referred to herein and constituting a part hereof, are illustrative of the invention but not restrictive thereof, and, together with the description, serve to explain the principles of the invention.

I claim:

1. A needleless transfer system capable of transferring a liquid without the utilization of a needle, the needleless transfer system comprising:
   a. a valve mechanism capable of selective mechanical interfit with a container into which or from which a liquid is to be transferred, said valve mechanism comprising:
   (1) a hollow enclosure;
   (2) a hollow spike member having one end thereof structurally affixed to one end of said hollow structure in an airtight manner so as to allow for the selective flow of a liquid through said hollow spike member into or out of the interior of said hollow enclosure;
   (3) a hollow neck member having one end thereof structurally affixed in an airtight manner to the opposite end of said hollow enclosure affixed to said hollow spike member so as to allow for the selective flow of a liquid through said hollow neck member into or out of said hollow enclosure when said valve mechanism is in an open position;
   (4) a filter member positioned within said hollow enclosure having one end thereof structurally abut against the interior end of said hollow enclosure to which said hollow spike member is affixed wherein said filter member is of a resilient composition and capable of expanding back to its original shape after being compressed;
   (5) a washer member structurally affixed to the end of said filter member that is adjacent to the end of said hollow enclosure to which said hollow neck member is affixed;
   (6) a shaft member structurally affixed to said washer member so as to be in axial alignment with said hollow neck member and extending from the interior of said hollow enclosure into the interior of said neck member;
   (7) an indicator shaft structurally affixed to said shaft member so as to be in axial alignment with said shaft member;
   (8) coupling means formed on the exterior of said hollow neck member at the end of said hollow neck member not structurally affixed to said hollow enclosure;
   (9) means structurally affixed to the exterior of said hollow enclosure capable of selectively mechanically affixing said hollow enclosure to a container; and
   b. a syringe comprising a tip member, plunger and cylindrical shaft member wherein there is formed about the interior portion of said cylindrical shaft member coupling means capable of mechanical interfit with the coupling means formed on the exterior of said hollow neck member such that upon the selective coupling of said syringe to said hollow neck member said washer member is caused to move axially with said shaft member and said indicator shaft so as to move away from the end of said hollow enclosure to which is affixed said hollow neck member thereby causing said valve mechanism to open.

2. A needleless transfer system capable of transferring a liquid without the utilization of a needle, as described in claim 1 wherein there is additionally formed through the wall of said hollow neck member a window element capable of allowing for the observing of the position of said indicator shaft within said hollow neck member.

3. A needleless transfer system capable of transferring a liquid without the utilization of a needle, as described in claim 2 wherein said indicator shaft has its exterior surface coated in two separate colors such that one is able to determine upon the viewing of a particular color through said window element whether or not said valve mechanism is in a closed or open position.

4. A needleless transfer system capable of transferring a liquid without the utilization of a needle, as described in claim 1 wherein said filter member is fabricated from nitrocellulose.

5. A needleless transfer system capable of transferring a liquid without the utilization of a needle, as described in claim 1 wherein said filter member is fabricated from cellulose acetate.

6. A needleless transfer system capable of transferring a liquid without the utilization of a needle, as described in claim 1 wherein said filter member is fabricated from nylon.

7. A needleless transfer system capable of transferring a liquid without the utilization of a needle, as described in claim 1 wherein said filter member is fabricated from polysulfane.

8. A needleless transfer system capable of transferring a liquid without the utilization of a needle, as described in claim 1 wherein said coupling means formed on the exterior of said hollow neck member comprises a threaded structure and the coupling means formed on the interior portion of said cylindrical shaft member of said syringe comprises a threaded structure capable of mechanical interfit with said threaded structure formed on the exterior of said hollow neck member.

9. A needleless transfer system capable of transferring a liquid without the utilization of a needle, as described in claim 1 wherein said means to affix said hollow enclosure comprises three clamp members each having an angular hooked member formed at the respective ends thereof.

10. A needleless transfer system capable of transferring a liquid without the utilization of a needle, as described in claim 1 wherein said filter member is fabricated from porous plastic material resilient in nature capable of allowing for the passage of a liquid medium therethrough.

11. A needleless transfer system capable of transferring a liquid without the utilization of a needle, the needleless transfer system comprising:
   a. a valve mechanism capable of selective mechanical interfit with a container into which or from which a liquid is to be transferred, said valve mechanism comprising:

(1) a hollow enclosure;

(2) a hollow spike member having one end thereof structurally affixed to one end of said hollow structure in an airtight manner so as to allow for the selective flow of a liquid through said hollow spike member into or out of the interior of said hollow enclosure;

(3) a hollow neck member having one end thereof structurally affixed in an airtight manner to the opposite end of said hollow enclosure affixed to said hollow spike member so as to allow for the selective flow of a liquid through said hollow neck member into or out of said hollow enclosure when said valve mechanism is in an open position;

(4) a filter member positioned within said hollow enclosure comprising a hollow cylindrical structure capable of being longitudinally compressed and having slits formed through its exterior wall so as to allow for the passage of a liquid therethrough;

(5) filtering material contained within said filter member;

(6) a washer member structurally affixed to the end of said filter member that is adjacent to the end of said hollow enclosure to which said hollow neck member is affixed;

(7) a shaft member structurally affixed to said washer member so as to be in axial alignment with said hollow neck member and extending from the interior of said hollow enclosure into the interior of said neck member;

(8) an indicator shaft structurally affixed to said shaft member so as to be in axial alignment with said shaft member;

(9) coupling means formed on the exterior of said hollow neck member at the end of said hollow neck member not structurally affixed to said hollow enclosure;

(10) means structurally affixed to the exterior of said hollow enclosure capable of selectively mechanically affixing said hollow enclosure to a container; and b. a syringe comprising a tip member, plunger and cylindrical shaft member wherein there is formed about the interior portion of said cylindrical shaft member coupling means capable of mechanical interfit with the coupling means formed on the exterior of said hollow neck member such that upon the selective coupling of said syringe to said hollow neck member said washer member is caused to move axially with said shaft member and said indicator shaft so as to move away from the end of said hollow enclosure to which is affixed said hollow neck member thereby causing said valve mechanism to open.

12. A needleless transfer system capable of transferring a liquid without the utilization of a needle, as described in claim 11 wherein there is additionally formed through the wall of said hollow neck member a window element capable of allowing for the observing of the position of said indicator shaft within said hollow neck member.

13. A needleless transfer system capable of transferring a liquid without the utilization of a needle, as described in claim 12 wherein said indicator shaft has its exterior surface coated in two separate colors such that one is able to determine upon the viewing of a particular color through said window element whether or not said valve mechanism is in a closed or open position.

14. A needleless transfer system capable of transferring a liquid without the utilization of a needle, as described in claim 11 wherein said filtering material comprises nitrocellulose.

15. A needleless transfer system capable of transferring a liquid without the utilization of a needle, as described in claim 11 wherein said filtering material comprises glass paper.

16. A needleless transfer system capable of transferring a liquid without the utilization of a needle, as described in claim 11 wherein said coupling means formed on the exterior of said hollow neck member comprises a threaded structure and the coupling means formed on the interior portion of said cylindrical shaft member of said syringe comprises a threaded structure capable of mechanical interfit with said threaded structure formed on the exterior of said hollow net member.

17. A needleless transfer system capable of transferring a liquid without the utilization of a needle, as described in claim 11 wherein said means to affix said hollow enclosure comprises three clamp members each having an angular hooked member formed at the respective ends thereof.

* * * * *